US011093033B1

(12) United States Patent
Wang et al.

(10) Patent No.: US 11,093,033 B1
(45) Date of Patent: Aug. 17, 2021

(54) IDENTIFYING OBJECT OF USER FOCUS WITH EYE TRACKING AND VISUALLY EVOKED POTENTIALS

(71) Applicant: Facebook, Inc., Menlo Park, CA (US)

(72) Inventors: Yu-Te Wang, San Diego, CA (US); Mark Allan Chevillet, Redwood City, CA (US)

(73) Assignee: Facebook, Inc., Menlo Park, CA (US)

( * ) Notice: Subject to any disclaimer, the term of this patent is extended or adjusted under 35 U.S.C. 154(b) by 0 days.

(21) Appl. No.: 16/666,282

(22) Filed: Oct. 28, 2019

(51) Int. Cl.
| | |
|---|---|
| *G09F 5/00* | (2006.01) |
| *G06F 3/01* | (2006.01) |
| *A61B 5/00* | (2006.01) |
| *G06T 11/00* | (2006.01) |
| *G06T 3/60* | (2006.01) |
| *G06T 7/70* | (2017.01) |
| *A61B 5/291* | (2021.01) |
| *A61B 5/378* | (2021.01) |

(52) U.S. Cl.
CPC .............. *G06F 3/013* (2013.01); *A61B 5/291* (2021.01); *A61B 5/378* (2021.01); *A61B 5/6803* (2013.01); *G06T 3/60* (2013.01); *G06T 7/70* (2017.01); *G06T 11/001* (2013.01); *G06F 3/015* (2013.01); *G06T 2207/30201* (2013.01)

(58) Field of Classification Search
CPC ........... G06F 3/013; G06F 3/015; G06T 3/60; G06T 7/70; G06T 11/001; G06T 2207/30201; A61B 5/0478; A61B 5/6803; A61B 5/04842; A61B 5/291; A61B 5/378
See application file for complete search history.

(56) References Cited

U.S. PATENT DOCUMENTS

| | | | | |
|---|---|---|---|---|
| 2005/0094099 | A1* | 5/2005 | Newman | A61B 3/0058 351/205 |
| 2008/0255949 | A1* | 10/2008 | Genco | A61B 5/165 705/14.4 |
| 2013/0127708 | A1* | 5/2013 | Jung | G06F 3/015 345/156 |
| 2013/0138248 | A1* | 5/2013 | Mathan | G06F 3/015 700/258 |

(Continued)

OTHER PUBLICATIONS

Wang, Y. et al. "Measuring Steady-State Visual Evoked Potentials from Non-Hair-Bearing Areas." 34th Annual International Conference of the IEEE EMBS, Aug. 28-Sep. 1, 2012, pp. 1806-1809.

*Primary Examiner* — Adam J Snyder
(74) *Attorney, Agent, or Firm* — Fenwick & West LLP

(57) ABSTRACT

A brain computer interface system includes a wearable interface, an eye tracking device, and a client device for determining what object a user is looking at on an electronic display. The client device determines a region on the electronic display based on an estimated user gaze direction received from the eye tracking device. For each virtual object in the gaze region, the client device displays a visual stimulus with a unique frequency. The client device receives from the wearable interface an electrical potential signal measured at the user's brain and evoked by a visual stimulus on the electronic display. The client device identifies the object in the gaze region with a stimulus frequency matching a frequency derived from the potential signal, and executes instructions relating to the object.

20 Claims, 9 Drawing Sheets

(56) References Cited

U.S. PATENT DOCUMENTS

| | | | | |
|---|---|---|---|---|
| 2014/0058483 | A1* | 2/2014 | Zao | A61B 5/04842 |
| | | | | 607/88 |
| 2015/0070262 | A1* | 3/2015 | Peters | G06F 3/013 |
| | | | | 345/156 |
| 2016/0077547 | A1* | 3/2016 | Aimone | G06F 3/015 |
| | | | | 345/8 |
| 2016/0187976 | A1* | 6/2016 | Levesque | G06F 3/016 |
| | | | | 705/14.4 |
| 2017/0287447 | A1* | 10/2017 | Barry | G06F 3/013 |
| 2017/0365101 | A1* | 12/2017 | Samec | A61B 3/09 |
| 2019/0250408 | A1* | 8/2019 | Laton | A61B 3/0058 |
| 2020/0097076 | A1* | 3/2020 | Alcaide | G06F 3/015 |

* cited by examiner

230

340

Low Frequency Blink
515

High Frequency Blink
525

Spinning Spiral
535

Spinning Checkerboard
545

Growing and Contracting
555

IDENTIFYING OBJECT OF USER FOCUS WITH EYE TRACKING AND VISUALLY EVOKED POTENTIALS

BACKGROUND

This disclosure relates generally to brain computer interface systems, and specifically to a brain computer interface system operable to identify what object a user is looking at on an electronic display.

Communication via physical actions, such as textual entry or manipulation of a user interface on a mobile or other device is a key form of interaction amongst individuals today. Additionally, certain online systems, such as online social networks, thrive on the network of users that frequent the online social network on a consistent basis. One component of online social networks is the ability of a user to interact with objects (e.g., electronically provided content) in an online or virtual setting. In many scenarios, detection of interactions requires the user to type or enter words and phrases through a physical means (e.g., a keyboard or clicking on a virtual keyboard) and/or to audibly provide commands. Physically entering words and phrases or providing audible commands may be cumbersome or impossible for certain individuals. Additionally, and more generally, physical entry of words and phrases for all individuals is often an inefficient way to communicate, as typing or otherwise manipulating various user interfaces can be cumbersome.

Eye tracking devices are being explored in relation to some of these problems. Eye tracking devices can be used to approximate a user's gaze direction and determine where the user is looking on a display. However, eye tracking devices in isolation provide imprecise estimations of a user's gaze direction. As a result, isolating where a user is looking on a complicated user interface (such as those described above) can be inaccurate. For example, when there are many small and/or tightly grouped interactable virtual objects the eye tracking device may frequently indicate the user is looking at the wrong object or that the user is not looking at an object when they are.

Additionally, Brain computer interface (BCI) systems are being explored in relation to some of these problems. BCI systems can be used match the frequencies of several visual stimuli on a display to a visually evoked potential frequency measured at the user's brain. The stimulus with the matching frequency can then be used to infer where a user is looking on the display. However, displaying a visual stimulus for each interactable object on a display can result in a user interface that is not aesthetically pleasing or is unpleasant to a user. Additionally, each stimulus must have a unique frequency relative to the other stimuli. With a complex user interface, it may not be possible to display a stimulus for each interactable object on the display such that the stimuli evoke distinguishable potential frequencies at the user's brain.

SUMMARY

Disclosed herein are systems and methods for enabling a user to interact with a virtual object on an electronic display by directing their gaze at the object. Generally, a system interprets an individual's eye movement and brain activity to characterize intentions of the individual in interacting with content on an electronic display. In particular embodiments, the system includes a wearable interface, an eye tracking device, and a client device including an electronic display. The wearable interface, the eye tracking device, and the client device are coupled to each other and to other electronics providing power and/or computing functionality. The wearable interface is also configured to be worn at a head region of a user, although in various embodiments the wearable interface, the eye tracking device, and the client device are integrated into a single device and worn at the head region of the user.

Embodiments also relate to an electrophysiological monitoring system which is a component of the wearable interface. The electrophysiological monitoring system includes a plurality of recording electrodes operable to detect and measure visually evoked potentials from the brain of the user. In particular, the electrophysiological monitoring system is configured to measure the frequency of visually evoked potentials at the head region of the user and transmit these frequencies to other components of the system.

Embodiments also relate to a method performed on the client device for determining which object a user is looking at on the electronic display. The client device receives an estimated user gaze direction from the eye tracking device and determines a point of gaze on the electronic display based on the gaze direction. The point of gaze is used by the client device to identify a gaze region on the electronic display. For each interactable virtual object in the gaze region, the client device displays a visual stimulus with a unique frequency relative to the other visual stimuli simultaneously being displayed. At a short time after beginning to display the visual stimuli, the client device receives one or more visually evoked potential signals measured at the head region of the user. The client device compares a frequency derived from the one or more potential signals to each of the frequencies of the visual stimuli and identifies a matching visual stimulus frequency. Interpreting the interactable virtual object corresponding to the matching visual stimulus frequency as the object the user is looking at, the client device executes instructions associated with the object.

Figure 1:
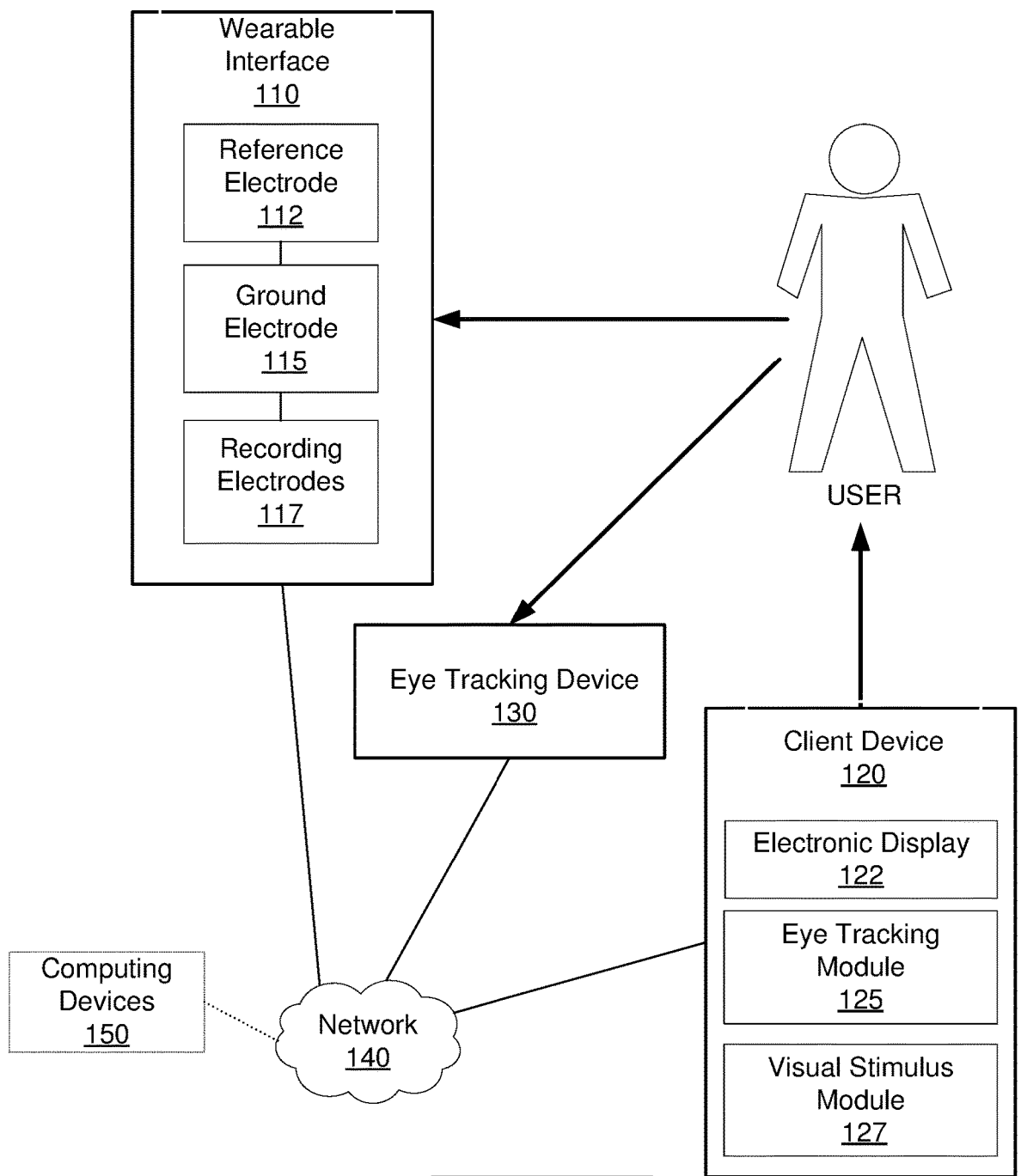
FIG. 1 illustrates a block diagram of a system for determining what object a user is looking at on an electronic display based on detecting and decoding brain activity of the user, in accordance with one or more embodiments.

The figures depict various embodiments for purposes of illustration only. One skilled in the art will readily recognize from the following discussion that alternative embodiments of the structures and methods illustrated herein may be employed without departing from the principles described herein.

DETAILED DESCRIPTION

1. Overview

Embodiments relate to a client device coupled to an eye tracking device and a wearable brain computer interface (BCI) including electrodes configured to receive visually evoked signals from a body region of the user. The client device includes an electronic display configured to display interactable virtual objects at various frequencies. The eye tracking device is operable to estimate the gaze direction of the user. The wearable interface, the client device, and the eye tracking device are coupled to other electronics providing power and/or computing functionality. The wearable interface is designed to be worn at a head region of a user and to characterize brain activity of the user, where decoded brain activity can be used as inputs to control other systems and/or electronic content provided to the user.

In relation to brain activity sensing, embodiments also relate to an electrophysiological monitoring system including recording electrodes, a ground electrode, and a reference electrode which enable measurement of the frequency of visually evoked potentials. Some embodiments of the electrophysiological monitoring system may include fewer or additional electrodes. Visually evoked potentials are electrical potentials recorded from a specific part of the human nervous system following presentation of a visual stimulus that excites photoreceptors in the retina on the human eye. In this electrophysiological system, visually evoked potential signals are determined relative to the reference electrode.

In relation to wearability, embodiments also relate to a wearable component that interfaces the electrodes and other system components to the head region of the user during use, in order to assess brain activity in a portable manner. In some embodiments, the wearable component may include one or both of the client device and the eye tracking device. For example, the wearable component may be a virtual reality (VR) or augmented reality (AR) headset.

In relation to eye tracking, embodiments also relate to an optical eye tracking device which receives images of a user's eye and uses them to infer the direction of user gaze. In the embodiments discussed herein, the user's head is either in a fixed position and orientation relative to the eye tracking device or the eye tracking device is provided with real-time updates of the user's relative head position and orientation.

In relation to virtual object interaction, embodiments also relate to a client device capable of identifying virtual objects on an electronic display in a pixel region determined by the user's gaze direction. Additionally, the client device is capable of displaying each virtual object in a determined region with a visual stimulus at a unique frequency relative to the stimuli of other objects in the region. The client device is also capable of receiving one or more visually evoked potential signals measured by the wearable interface, and identifying an object with a visual stimulus frequency matching a frequency derived from the one or more signals among the objects in the pixel region. Upon identifying a match, the client device is operable to execute instructions corresponding to an interaction with the identified object.

2. System Environment

FIG. 1 is a block diagram of a system 100 for executing instructions corresponding to a virtual object on an electronic display by detecting and decoding brain activity of a user, in accordance with one or more embodiments. The system 100 includes a client device 120 that is coupled via a network 140 to an eye tracking device 130 and a wearable interface 110. In some embodiments, the components of system 100 are integrated into a single device and connected directly through hardware components of the device. The client device 120 is configured to receive user gaze direction estimations from the eye tracking device 130 and visually evoked potential frequency measurements from the wearable interface 110. The network 140 is connected to additional computing devices 150 capable of performing additional processing on outputs from the eye tracking device 130 and wearable interface 110 as well as interacting with the client device 120.

The components of system 100 are designed to be used concurrently by a user. Wearable interface 110 is positioned and retained at the head region of the user and includes reference electrode 112, ground electrode 115, and recording electrodes 117. In some embodiments, the eye tracking device 130 is a component of the client device 120. In other embodiments, the wearable interface 110, the client device 120, and the eye tracking device 130 are integrated components of a single device positioned and retained at the head region of the user.

The wearable interface 110, with recording electrodes 117, is configured to enable characterization of brain activity from one or more regions of the user's brain through a non-invasive method. Specifically, each of the one or more recording electrodes 117 form a channel with reference electrode 112. Each channel represents the difference in measured electrical potential between the corresponding recording electrode and the reference electrode 112. The ground electrode 115 removes electrical potential noise measured globally by each electrode in the system. In some embodiments, the various electrodes included on the wearable interface 110 are wet electrodes, where an electrolyte gel is in contact with both the electrode and the user. In other embodiments, the various electrodes included on the wearable interface 110 are dry electrodes. In the same or different embodiments, wearable interface 110 detects steady state visually evoked potentials (SSVEP), where the frequency of the visually evoked potentials remains uniform while evoked by a particular visual stimulus with a particular frequency.

Eye tracking device 130 is configured to continuously determine the direction of user gaze as the user's eyes move. Although any eye tracking device could be used, the embodiments described herein are generally directed towards non-invasive optical tracking methods. In some embodiments, the eye tracking device 130 uses video-based tracking methods, where a camera receives images of a user's eyes. In the same or different embodiments, eye movement is determined from collected images by using the corneal reflection and the center of the pupil as features tracked over time. In still other embodiments, the eye tracker is used in combination with a functional near-infrared spectroscopy (fNIRS) monitoring system positioned at the head region of the user to measure neuroactivity. For example, the fNIRS monitoring system can be used to detect when regions of the primary motor cortex activate, suggesting a user might be moving their eyes, prompting eye tracking device 130 to begin capturing images of the user's eyes. In some embodiments, the eye tracking device is a component of a head-mounted display worn by the user.

Client device 120 includes electronic display 122, eye tracking module 125, and visual stimulus module 127. Electronic display 122 is configured to display graphical content on an array of pixels, including virtual interactable objects. Eye tracking module 125 is configured to map a user gaze direction received from eye tracking module 130 to a pixel position on electronic display 122. Visual stimulus module 127 is configured to augment objects displayed by electronic display 122 with visual stimuli at distinct frequencies. In particular, objects simultaneously augmented with visual stimuli by visual stimulus module 127 each have a unique stimulus frequency relative to each other. Visual stimulus module 127 is also configured to receive visually evoked potential frequencies detected by wearable interface 110 and compare received frequencies to the frequencies of objects on electronic display 122 currently augmented with visual stimuli.

The electronic display 122 is a graphical display capable of rendering virtual content as an array of pixels. Example electronic displays include televisions, computer monitors, projectors, and mobile device touch screens. In some embodiments, client device 120 is a VR or AR headset and electronic display 122 is affixed to the headset on the inner portion of a component that is placed over the user's eyes. In other embodiments, client device 120 is a smart watch, such as an Apple Watch, and electronic display 122 is the face of the smart watch.

While the client device 120 of the system can be implemented onboard the wearable components of the system 100, the client device 120 can additionally or alternatively be supported by or in communication with other computing devices 150 and/or a user device, for instance, through the network 140. Examples of computing devices 150 and/or user devices include a personal computer (PC), a desktop computer, a laptop computer, a notebook, a tablet PC executing an operating system, for example, a Microsoft Windows-compatible operating system (OS), Apple OS X, and/or a Linux distribution. In other embodiments, the computing devices and/or user devices can be any device having computer functionality, such as a personal digital assistant (PDA), mobile telephone, smartphone, wearable computing device, or any other suitable computing device. The client device 120 and/or other computing devices can execute instructions (e.g., computer code) stored on a computer-readable storage medium in order to perform the steps and processes described herein for enabling control of other systems by a user through user eye gaze. Collectively, the client device 120 and any other computing devices, with the network 140, can operate as a computing system for implementation of methods according to specific applications of use of the system 100. Generally, the computing system determines intentions of the user from signals provided by the wearable interface 110, where the intentions describe user wishes in relation to interacting with virtual objects displayed by the electronic display 122.

The network 140 facilitates communications between the one or more computing devices. The network 140 may be any wired or wireless local area network (LAN) and/or wide area network (WAN), such as an intranet, an extranet, or the Internet. In various embodiments, the network 140 uses standard communication technologies and/or protocols. Examples of technologies used by the network 140 include Ethernet, 802.11, 3G, 4G, 802.16, or any other suitable communication technology. The network 140 may use wireless, wired, or a combination of wireless and wired communication technologies. Examples of protocols used by the network 140 include transmission control protocol/Internet protocol (TCP/IP), hypertext transport protocol (HTTP), simple mail transfer protocol (SMTP), file transfer protocol (TCP), or any other suitable communication protocol.

3. Eye Tracking 3.1 System—Eye Tracking Device Coupled to Client Device

Figure 2A:
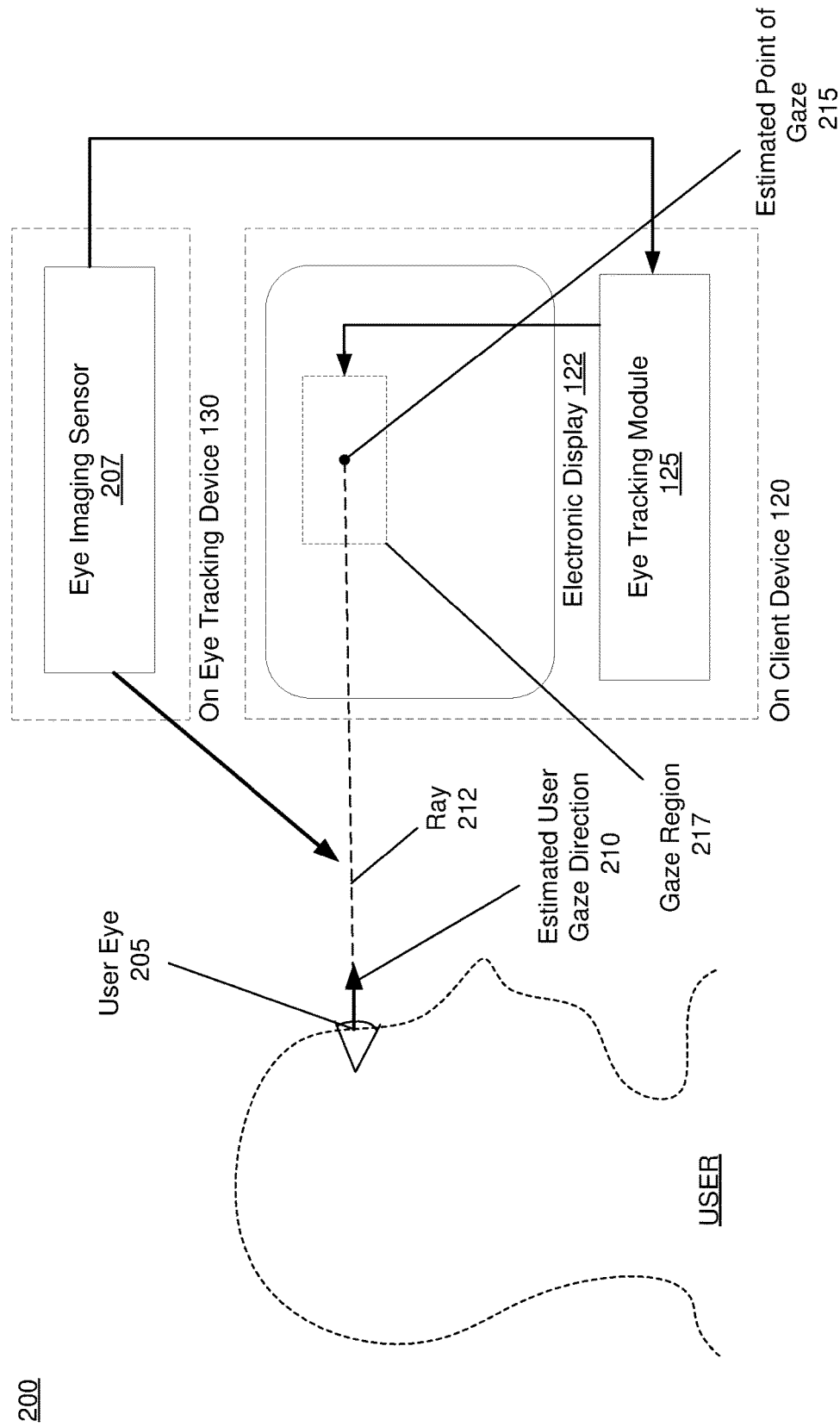
FIG. 2A illustrates a system operable to map a user's gaze to a region on an electronic display using an eye tracking device, in accordance with one or more embodiments.

FIG. 2A depicts an eye tracking system 200 performing a technique to map user gaze to a region on an electronic display component of a client device, in accordance with one or more embodiments. The electronic display 122 coupled to client device 120 is positioned in a location relative to the user such that the user directs their gaze at the electronic display. The eye tracking device 130 coupled to client device 120 is positioned in a location relative to the user such that the eye tracking device 130 has a view of the user's eye 205.

Eye tracking device 130 includes computer components operable to perform logical operations on data captured by eye imaging sensor 207 and transmit data to other components of system 200. In various embodiments, eye tracking device 130 is connected to the network through wired or wireless components. In the wired case, eye tracking device 130 may include one or more exterior ports for inserting cables, such as one or more exterior universal serial bus (USB) ports, to connect to other devices in system 200. In the wireless case, eye tracking device 130 may include wireless receiver components, such as a W-Fi or Bluetooth receiver, to connect to other devices in system 200. In other embodiments, eye tracking device 130 is an integrated component of client device 120. For example, client device 120 may be a VR or AR head set worn by the user that includes eye tracking device 130. In this case, eye tracking device 130 is coupled to client device 120 through internal hardware components of client device 120.

Eye imaging sensor 207 is an integrated component of eye tracking device 130 configured to capture images of the user's eye 205 at a high enough capture rate to allow live estimation of user gaze direction. For example, eye imaging sensor 207 may capture images of user eye 205 at frequencies ranging from 30 Hz to 1,250 Hz, depending on the required imaging speed for a given embodiment. In some embodiments, eye imaging sensor 207 is configured to capture infrared or near-infrared images.

As described in section 2, client device 120 can execute instructions (e.g., computer code) stored on a computer-readable storage medium in order to perform the steps and processes relevant for processing eye tracking information received from eye tracking device 130 through a network connection. In particular, client device 120 stores computer-code related to an eye tracking module 125. Eye tracking module 125 is configured to receive data transmitted by eye tracking device 130 and perform logical operations to process the received data. Additionally, eye tracking module 125 is configured to interface with other components of client device 120 in order to transmit processed data, execute instructions, or otherwise interact with the system.

3.2 Method—Identifying User Gaze Region on Electronic Display

Figure 2B:
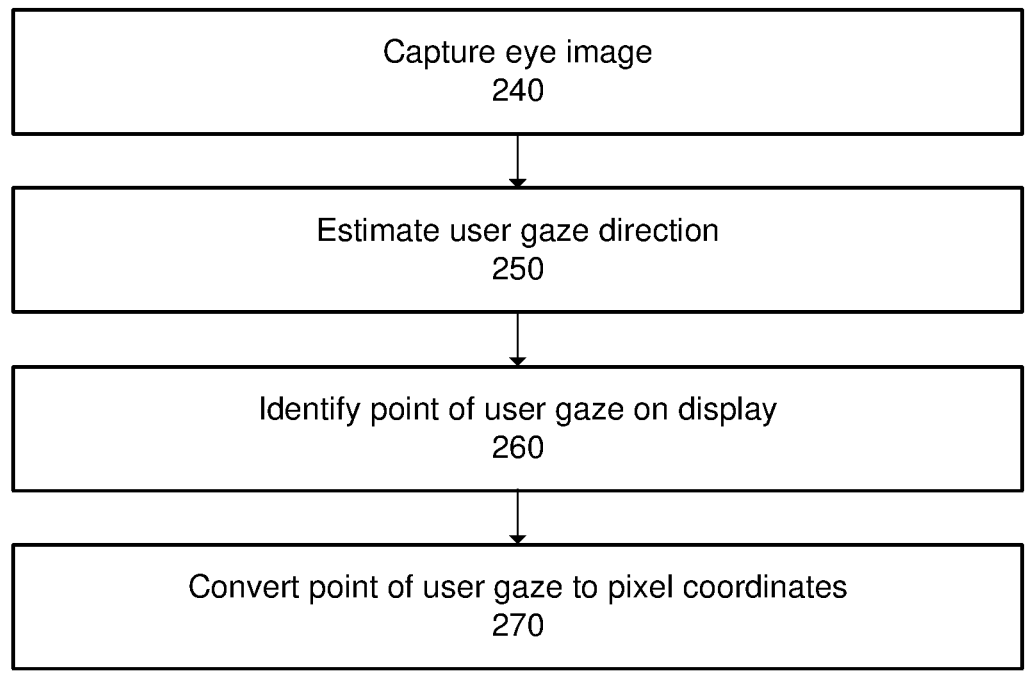
FIG. 2B illustrates a flow chart for mapping a user's gaze to a region on an electronic display, in accordance with one or more embodiments.

FIG. 2B is a flowchart 230 showing the sequence of actions taken by system 200 in FIG. 2A to identify a region on the electronic display 130 which contains a virtual object the user is currently looking at (i.e. directing their gaze at). Eye tracking device 205 captures 240 an image of the user's eye using eye imaging sensor 207. Using the user eye image, eye tracking device 205 estimates the user's gaze direction 210. Estimated user gaze direction 210 is represented in a coordinate frame relative to eye tracking device 130. For example, estimated user gaze direction 210 can be represented as a normalized three-dimensional vector originating at user eye 205. In some embodiments, eye tracking device 207 determines the direction of user gaze based on light reflections on user eye 205 detected in the captured images. In the same or different embodiments, the eye tracking device 139 determines the direction of user gaze based on corneal reflections created by using the center of the pupil and infrared non-collimated light reflections detected in the captured images.

Eye tracking module 125 on client device 120 receives an estimated user gaze direction 210 and corresponding user eye 205 position from eye tracking device 130 at a regular interval. In particular, the estimated user gaze direction 210 and user eye 205 position are provided at a rate such that eye tracking module 125 has real time updates of user eye movement. Eye tracking module 125 converts the estimated user gaze direction 120 and user eye 205 position to a coordinate frame relative to the electronic display 122. In the coordinate frame relative to the electronic display 122, eye tracking module 125 projects a ray 212 from the user eye 205 position in estimated user gaze direction 210. Eye tracking module 125 identifies 260 the estimated point of gaze 215 on the electronic display 122 at the position where ray 212 intersects the electronic display 122. Eye tracking module 125 converts 270 the estimated point of gaze 215 to a two-dimensional pixel coordinate position on electronic display 122. Based on the pixel coordinates of estimated point of gaze 215, eye tracking module 125 identifies a gaze region 217 on electronic display 122 which encapsulates the pixel coordinates. In the case that ray 212 does not intersect electronic display 122, then eye tracking module 125 waits to receive subsequent input from eye tracking module 125 at the next regular interval.

The gaze region 217 is centered at the pixel coordinates and represented as a rectangle with a width and height in pixel coordinates. In alternative embodiments, the gaze region can be represented as a circle, a square, a triangle, or any other reasonable two-dimensional shape. In the same or different embodiments, the electronic display 122 may be broken into pre-defined regions, and the gaze region 217 is determined as the pre-defined region that point of gaze 215 is within. In further embodiments, the gaze region 215 is determined based on the user's field of view. For example, gaze region 215 may be defined as a region captured by the fovea on the retina in the user's eyes. The fovea is responsible for sharp central vision (i.e. where the user's attention is directed to) and accounts for approximately 5 degrees of a user's field of view. As such, in this example the boundaries of the gaze region 215 could be positioned around the point of gaze 217 to include 5 degrees of the user's field of view.

4. Identifying Objects Using Evoked Potential Frequencies 4.1 Method—Matching Visually Evoked Potential Frequency FIG. 3 depicts a BCI system 300 performing a technique to identify which virtual object on an electronic display a user is currently looking at by detecting steady state visually evoked potentials, in accordance with one or more embodiments. A steady state visually evoked potential (SSVEP) results from visual stimuli exciting photoreceptors in the retina, where the frequency of the evoked potential is the same as (or a multiple of) the stimulus frequency. SSVEP signals are generally strongest when evoked by stimuli at frequencies ranging from 3.5 Hz to 75 Hz, although signals can still be detected outside this range. The electronic display 122 coupled to client device 120 is positioned in a location relative to the user such that the user directs their gaze at the electronic display. The wearable interface 310 coupled to client device 120 is worn on the head region of the user such that it is operable to detect electrical potentials in the user's brain.

Wearable interface 310 functions to interface the head region of the user with an electrophysiological monitoring system (described in more detail below), in order to assess brain activity in a portable manner. A flexible retaining band fixes wearable interface 310 to the head region of a user. In alternative embodiments, the wearable interface is worn as a cap placed over the top of the user's head. In still another embodiment, the client device 120 is itself a wearable device and wearable interface 310 is a component of client device 120. For example, the client device 120 can be a VR or AR headset, as discussed above.

Wearable interface 310 includes computer components operable to perform logical operations on data captured by the electrophysiological monitoring system and transmit data to other components of system 300. Wearable interface 310 is coupled to client device 120 through a network connection. In various embodiments, wearable interface 310 is connected to the network through wired or wireless components. In the wired case, wearable interface 310 may include one or more exterior ports for inserting cables, such as one or more exterior universal serial bus (USB) ports, to connect to other devices in system 300. In the wireless case, wearable interface 310 may include wireless receiver components, such as a W-Fi or Bluetooth receiver, to connect to other devices in system 300. In embodiments where wearable interface 310 is a component of client device 120, as discussed above, wearable interface 310 is coupled to client device 120 through internal hardware components of client device 120.

The electrophysiological monitoring system of wearable interface 310 includes a plurality of electrodes that together continuously measure electrical potentials in the user's brain at millisecond intervals. Specifically, the electrophysiological system includes a plurality of recording electrodes 312, reference electrode 315, and ground electrode 317. Each individual recording electrode is connected to reference electrode 315 and forms a channel. The channel represents the difference in electrical potential measured by the recording electrode and the reference electrode. The ground electrode 317 is connected to the circuit formed by the recording electrodes 312 and reference electrode 315 such that electrical signals are filtered out from sources other than the user's brain, such as power line noise. The recording electrodes 312 are positioned on the wearable interface 310 such that they receive potential signals generated at the occipital cortex of the user's brain. For example, the recording electrodes could be placed on the back of the user's head, which is directly exterior to the occipital cortex. The reference electrode 315 and ground electrode 317 are each distinctly positioned on wearable interface 310 such that they each contact the user's head at a different region than any of the recording electrodes 312. In some embodiments, the electrophysiological monitoring system includes only recording electrodes 312 and reference electrode 315.

In one embodiment, the electrophysiological monitoring system of wearable interface 310 is an electroencephalogram (EEG) system. In this case, each recording electrode is connected to one input of a differential amplifier and the reference electrode 315 is connected to the other input of each differential amplifier. The differential amplifiers amplify the measured voltage difference between each recording electrode and the reference electrode. The electrodes used in the EEG system can be any electrode capable of measuring electrical potentials in the user's brain with a millisecond time resolution. Example electrodes include wet or dry individual disposable EEG electrodes, wet or dry individual reusable EEG electrodes, wet or dry EEG electrode caps, and EEG needle electrodes.

Client device 120 is operable to display interactable virtual objects on electronic display 122. Each object's associated interactions, and the operations resulting from the interactions, are determined by computer-code stored on client device 122. Example interactable virtual objects include buttons, shapes, video game characters, and any other interactable elements of a user interface.

The electronic display 122 is operable to alter the pixels displaying virtual content to produce a visual stimulus at a frequency between 1 Hz and 60 Hz or above. For example, the electronic display can blink a group of pixels on the screen at a particular frequency. In this case, blinking refers to pixels alternating between two colors. In some embodiments, the pixels alternate between two colors at a high enough frequency that the blinking is imperceptible to the user. In this case, the user perceives the stimulus as a single color (i.e. a blend of the two colors). Colors blinking at a frequency of 50 Hz or more are generally perceived this way by a human user, however perception can vary from person to person. In other embodiments, the electronic display can spin a polychromatic shape represented by a group of pixels, such as a circular checkerboard or a spiral.

Client device 120 stores computer-code related to a visual stimulus module 330, which is a specific embodiment of visual stimulus module 127 in FIG. 1. Visual stimulus module 330 is configured to receive data transmitted by wearable interface 310 and perform logical operations to process the received data. Additionally, visual stimulus module 330 is configured to interface with other components of client device 120 in order to transmit processed data, execute instructions, or otherwise interact with the system.

4.2 Method—Matching Visually Evoked Potential Frequency

Figure 3A:
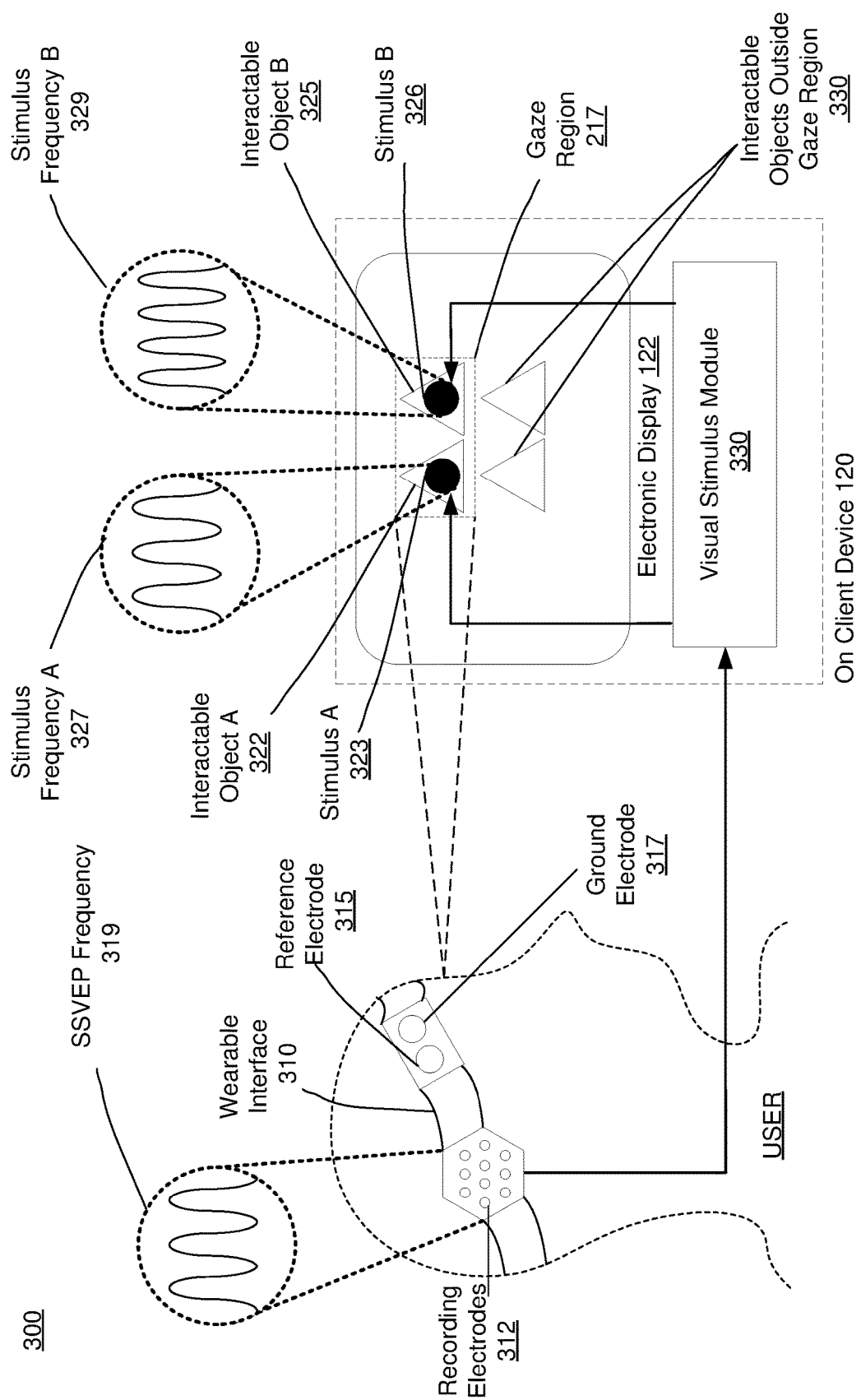
FIG. 3A illustrates a BCI system operable to identify the object a user is looking at on an electronic display using a wearable electrophysiological monitoring system, in accordance with one or more embodiments.
Figure 3B:
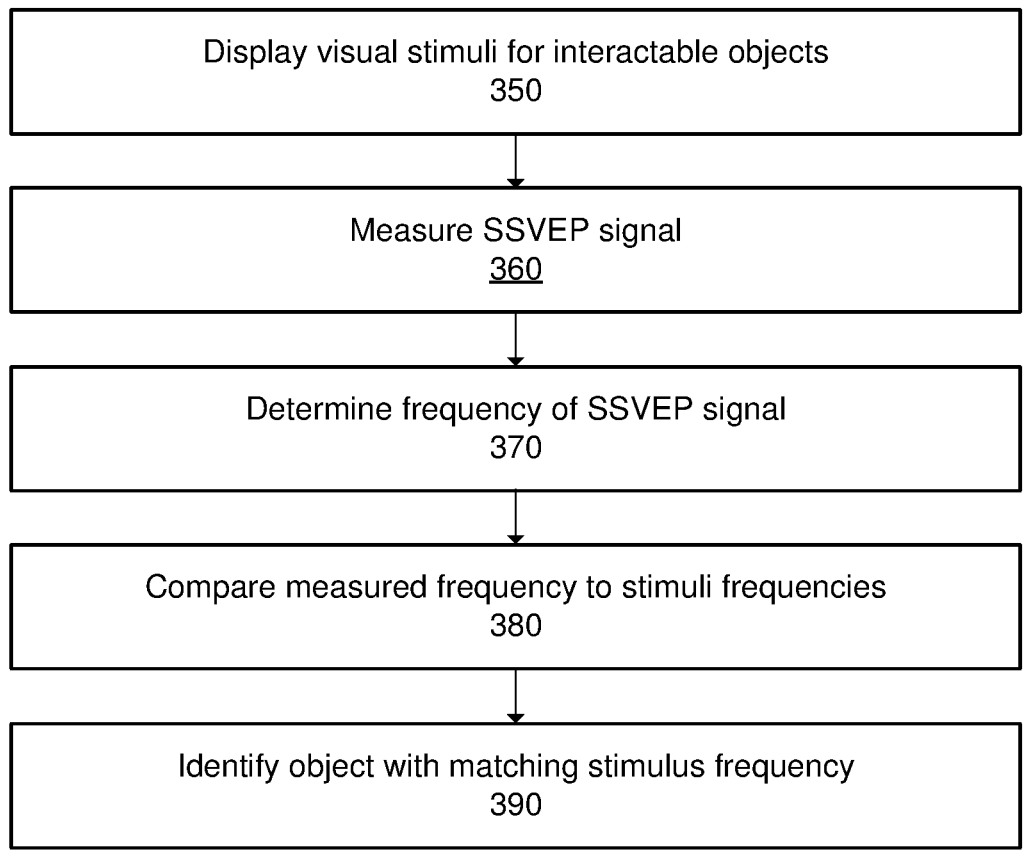
FIG. 3B illustrates a flow chart for identifying the object a user is looking at on an electronic display, in accordance with one or more embodiments.

FIG. 3B is a flowchart 340 showing the sequence of actions taken by system 300 in FIG. 3A to identify which virtual object the user is currently looking at (i.e. directing their gaze at) on an electronic display. Visual stimulus module 330 receives information defining a gaze region 217 on electronic display 122 from eye tracking module 125. Gaze region 217 includes two interactable virtual objects, interactable object A 322 and interactable object B 325. However, the gaze region 217 may include any number of interactable objects. The interactable objects outside the gaze region 330 are not considered. Visual stimulus module 330 displays 350 a visual stimulus A 323 for interactable object A 322 at stimulus frequency A 327. Similarly, visual stimulus module 330 displays 350 a visual stimulus B 326 for interactable object B 325 at stimulus frequency B 329. As described above, in some embodiments visual stimulus frequency A 327 and visual stimulus frequency B 329 may be evoked by respectively blinking the pixels comprising stimulus A 323 and stimulus B 326. In other embodiments, stimulus frequency A 327 and stimulus frequency B 329 may be evoked by spinning a polychromatic shape represented by a respective subset of the pixels comprising stimulus A 323 and stimulus B 326. In some embodiments, the stimulus frequencies are chosen such that no frequencies are part of the same harmonic series.

The possible frequencies to be used by the visual stimulus module 330 is limited by the refresh rate of the electronic display 122. That is, for an electronic display 122 with a refresh rate of 120 Hz, an interactive object may be stimulated with a frequency of 60 Hz or less. Moreover, since the electronic display 122 displays images with discrete time durations, the frequencies at which an interactive object may be stimulated are also discrete. For example, the frequency at which an interactive object may be stimulated is equal to refresh rate $$\text{refresh\_rate}/k, \; k=2,3,\ldots$$

Where refresh rate is the refresh rate of the electronic display 122 and k is an integer larger or equal to 2.

The channels formed by recording electrodes 312 on wearable interface 310 measure 360 a steady state visually evoked potential (SSVEP) signal at some time in milliseconds after visual stimulus module 330 begins displaying visual stimuli for interactable object A and interactable object B. Wearable interface 310 transmits the SSVEP signal to visual stimulus module 330 through the network connection.

Upon receiving the SSVEP signal, visual stimulus module 330 determines 370 the frequency of the signal. In particular, visual stimulus module 330 performs Fourier analysis on the detected potential signal to transform the potential signal from a time domain to a frequency domain. In one embodiment, visual stimulus module 330 only considers a signal detected at one recording electrode and uses the Fast Fourier Transform (FFT) algorithm to perform Fourier analysis. In other embodiments, the visual stimulus module 330 considers the simultaneous signals detected at multiple recording electrodes and uses Fourier analysis algorithms capable of processing signals from multiple channels. For example, visual stimulus module 330 may separately determine the frequency of signals measured at multiple recording electrodes using FFT and then compute a single dominant frequency as an aggregation of each determined frequency (e.g. the mode or mean frequency). In some embodiments, a voting scheme is used to select a single dominant frequency from a set of frequencies derived from a set of signals measured at multiple recording electrodes. For example, the voting scheme selects the frequency that is present in the most number of signals. As another example, visual stimulus module 330 may use a canonical correlation analysis (CCA) method to filter signals measured at multiple recording electrodes into one signal, and then determine the frequency of the signal using FFT.

Visual stimulus module 330 compares 380 visually evoked potential frequency 319 to both visual stimulus frequency A 327 and visual stimulus frequency B 329. In this case, visual stimulus module 330 determines that SSVEP frequency 319 matches stimulus frequency A. Given the match, visual stimulus module 330 identifies 390 interactable object A as the object the user is looking at. In one embodiment, if FFT analysis of the signal produces multiple harmonic frequencies (discussed below), visual stimulus module 330 selects the frequency with the greatest amplitude as SSVEP frequency 319. Although as depicted in FIG. 3 SSVEP frequency 319 and stimulus frequency 327 are an exact match, in practice SSVEP frequency 319 as measured may be noisy and require processing by visual stimulus module 330 to estimate a single frequency. For example, visual stimulus module 330 may determine the correlation between a measured signal and each of a set of signal templates corresponding to specific frequencies (i.e. 8 Hz, 9 Hz, 10 Hz, etc.) and select the frequency corresponding to the template with the highest correlation to be SSVEP frequency 319. In some embodiments, visual stimulus module 330 may use a frequency similarity threshold to determine whether an SSVEP frequency and a stimulus frequency match.

In response to determining that the user is looking at interactable object A 322, visual stimulus module 330 provides this information to other software components of client device 120. In particular, client device 120 provides the information to a software component of client device 120 associated with the interactable objects currently displayed by electronic display 122 to execute instructions corresponding to an interaction with interactable object A 322. Example software components of client device 120 include a video game, an application menu, an internet browser, or any other software component with a user interface.

5. Method—Virtual Object Interaction by User Gaze

Figure 4:
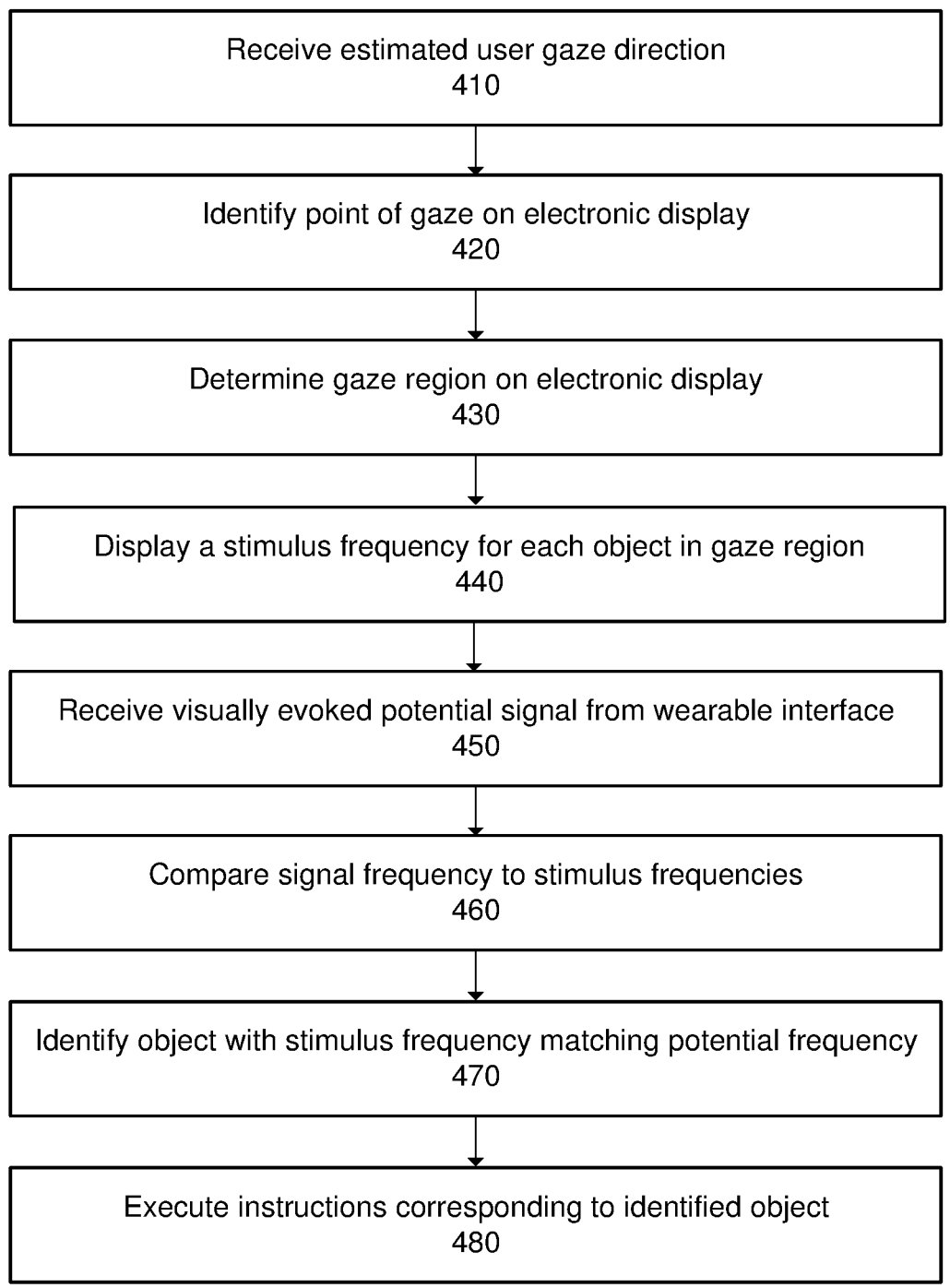
FIG. 4 illustrates a flow chart for determining which object a user is looking at on an electronic display using an eye tracking device and a BCI system, in accordance with one or more embodiments.

FIG. 4 is a flowchart 400 showing the sequence of actions that client device 120 depicted in FIG. 1 takes to determine which object a user is looking at on electronic display 122 and execute instructions corresponding to an interaction with the object, in accordance with one or more embodiments. Client device 120 receives 410 an estimated user gaze direction from eye tracking device 130 and identifies 420 the point of gaze on the electronic display 122 based on the gaze direction. Using the point of gaze, the client device 120 determines 430 a gaze region around the point of gaze on the electronic display 122 enclosing a set of virtual objects. For each object in the gaze region, the client device 120 displays 440 a visual stimulus at a unique frequency.

Client device 120 receives 450 a detected visually evoked potential signal from the wearable interface 110 worn by the user. The frequency of the potential signal is compared 460 to each stimulus frequency displayed by the objects in the gaze region to identify 470 an object displaying a stimulus frequency matching the signal frequency. Having identified the object, which is inferred to be the object the user is looking at, client device 120 executes instructions corresponding to an interaction with the identified object.

The method for identifying which object a user is looking at described above provides several benefits to both the system 100 and the user. By first identifying a gaze region on electronic display 122 with eye tracking device 130, the system 100 limits the number of interactable objects which must be simultaneously displayed with a unique stimulus to only those objects in the gaze region. As a result, client device 120 and its corresponding components can be configured to operate with fewer distinct frequencies. For example, the frame rate of the electronic display 122 can be lower since the number of available frequencies is limited by the frame rate. The comparison step performed by client device 120 is also faster because fewer comparisons are needed. Additionally, the frequencies of the stimuli displayed on electronic display 122 can be separated by larger increments on the frequency domain, making the potentially noisy visually evoked potential frequencies detected at the wearable interface 110 more easily distinguishable as one of the stimulus frequencies. Regarding the user experience, many objects simultaneously blinking or spinning on a user interface can be unattractive, disorienting, confusing, or upsetting to some users. Even if high frequency visual stimuli are used and a user cannot perceive the blinking, the user may still be made uncomfortable by too many simultaneous visual stimuli. As such, the methods described above help ensure a more pleasant and efficient user experience when interacting with virtual objects through gaze.

6. Example Visual Stimuli

Figure 5A:
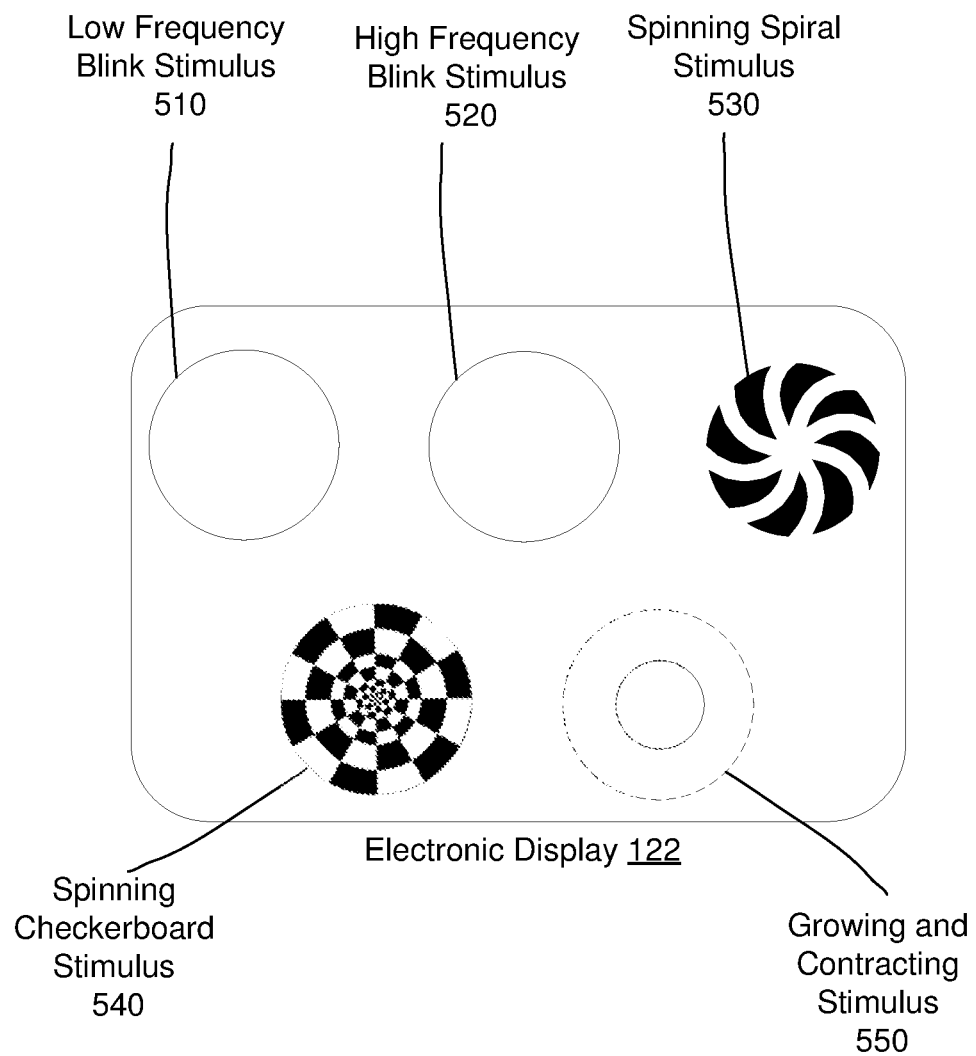
FIG. 5A illustrates several examples of visual stimuli corresponding to virtual objects on an electronic display, in accordance with more embodiments.
Figure 5B:
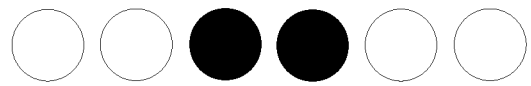
FIG. 5B illustrates how the visual stimuli depicted in FIG. 5A change over time, in accordance with one or more embodiments.
Figure 5B:
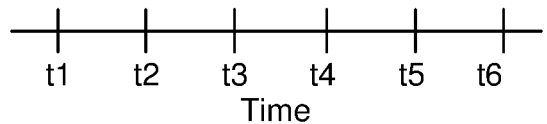
Figure 5B:
Figure 5B:
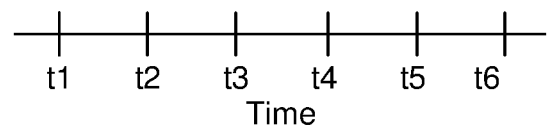
Figure 5B:
Figure 5B:
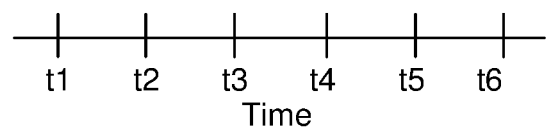
Figure 5B:
Figure 5B:
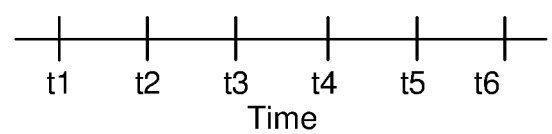
Figure 5B:
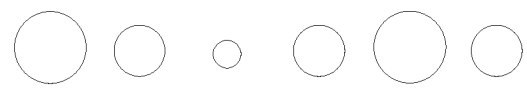
Figure 5B:
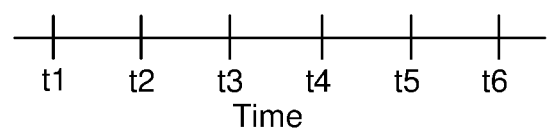

FIG. 5A and FIG. 5B illustrate several example visual stimuli corresponding to virtual objects displayed by electronic display 122, in accordance with more embodiments. The depicted visual stimuli vary by frequency range and potential evoking mechanism (e.g. blinking or movement). Which type of visual stimulus is displayed for a virtual object may vary across embodiments depending on system context. For example, the type of visual stimuli may be influenced by the specific type of client device 120, the user's environmental context, user interface aesthetics, electronic display 122 frequency capabilities, or wearable interface 110 measurement capabilities. For each type of visual stimulus discussed below, the frequency of the stimulus must generally be at least 3.5 Hz to evoke an SSVEP. The diagrams depicted in FIG. 5B each demonstrate how a corresponding visual stimulus in FIG. 5A changes over time. Time increments t1 to t6 are variables that depend on the specific embodiment and frequency of a given stimulus. In particular, increments t1 to t6 do not necessarily represent the same values between each diagram in FIG. 5B.

Object stimulus 510 shown on electronic display 122 uses a circle blinking at a low frequency to evoke steady state potentials in the user's brain. In this case, the steady state potential frequency in Hz corresponds to the rate at which the stimulus blinks (i.e. blinks per second). Low frequency blink diagram 515 depicts how object stimulus 510 changes over a sequence of time intervals t1 to t6. Low frequency is defined here as any frequency at which a user can perceive that the pixels comprising a stimulus are alternating between two colors. The exact frequencies at which a blink is perceptible to the user can vary by the user and display. For example, a blink can generally be perceived by a user when displayed through modulated light on a computer display at frequencies less than 50 Hz.

Object stimulus 520 shown on electronic display 122 uses a circle blinking at a high frequency to evoke steady state potentials in the user's brain. High frequency blink diagram 525 depicts how object stimulus 520 changes over a sequence of time intervals t1 to t6. High frequency is defined here as any frequency at which a user cannot perceive that the pixels comprising a stimulus are alternating between two colors, and instead perceives the stimulus as a single color. As with low frequency blinks, the exact frequencies at which a high frequency blink is perceptible to the user can vary by the user and display. For example, a blink generally cannot be perceived by a user when displayed through modulated light on a computer display at frequencies of 50 Hz or greater.

Object stimulus 530 shown on electronic display 122 uses a spinning polychromatic spiral to evoke steady state potentials in the user's brain. Unlike the blinking stimuli described above, the spiral stimulus evokes steady state visual potentials through the spiral's movement (i.e. rotation). In this case, the steady state potential frequency in Hz corresponds to the rate at which the spiral completes revolutions. Spinning spiral diagram 535 depicts how object stimulus 530 changes over a sequence of time intervals t1 to t6. The spiral spins at relatively low frequencies, as high frequencies result in the colors comprising the spiral being perceived as a single color by the user. As with blinking stimuli, the exact frequencies at which the spiral's individual colors are perceptible to the user can vary by the user and display. For example, a user can generally distinguish the colors comprising a spiral stimulus at frequencies less than 10 Hz.

Object stimulus 540 shown on electronic display 122 uses a spinning checkerboard to evoke steady state potentials in the user's brain. Spinning checkerboard diagram 545 depicts how object stimulus 540 changes over a sequence of time intervals t1 to t6. As with the spiral stimulus, the checkerboard stimulus evokes steady state visual potentials through the checkerboards' movement (i.e. rotation) and spins at relatively low frequencies.

Object stimulus 550 shown on electronic display 122 uses a growing and contracting circle to evoke steady state potentials in the user's brain. Growing and contracting diagram 555 depicts how object stimulus 550 changes over a sequence of time intervals t1 to t6. As with the other moving stimuli, the circle stimulus evokes steady state visual potentials through its movement (i.e. growing and contracting) and grows and contracts at relatively low frequencies.

Some visual stimuli induce harmonic SSVEP frequencies, while others do not. As used herein, a visual stimulus that induces harmonic SSVEP frequencies is a visual stimulus for which wearable interface 110 would measure an SSVEP frequency in response to the stimulus displayed with both a fundamental frequency and with a multiple of the fundamental frequency as the same potential frequency. Visual stimuli which evoke a linear SSVEP signal (e.g. a sinusoidal waveform) do not produce harmonics, as the signal is distinguishable as having a specific frequency. Visual stimuli which evoke non-linear SSVEP signals (i.e. noisy signals) produce multiple harmonic signals when analyzed with FFT. For example, if a stimulus with frequency f evokes an SSVEP signal, performing FFT on the signal may produce signals f, 2f, and 3f. In relation to the discussed stimuli, a polychromatic spiral stimulus does induce harmonics, while a checkerboard stimulus does not. Visual stimuli that do not induce harmonics allow for using frequencies that are multiples of each other without reducing the ability to distinguish objects. As such, a larger number of frequencies are available when displaying visual stimuli that do not induce harmonics.

Although circles and two colors are used to depict each of the object stimuli in FIG. 5, one skilled in the art will recognize that many stimulus shapes and color patterns are possible. In particular, any shape, number of colors, and color pattern which evokes steady state potentials in a user's brain can be used for displaying stimuli on electronic display 122.

7. Electrode Configuration

Figure 6A:
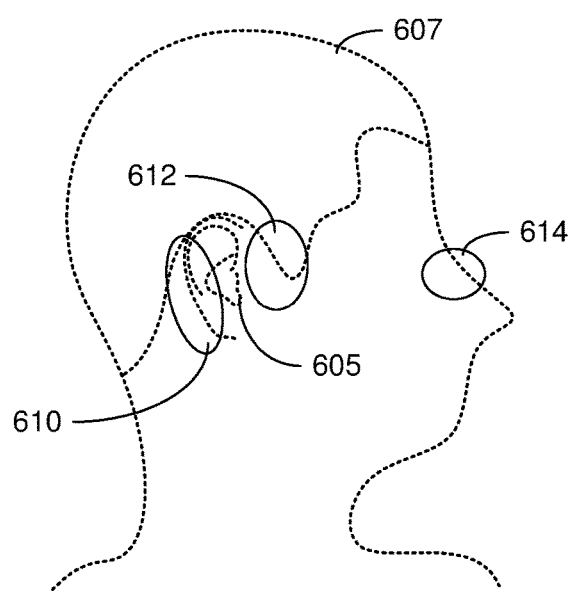
FIG. 6A illustrates regions in which dry electrodes may be placed for recording electrophysiological signals, in accordance with one or more embodiments.

Although the strongest SSVEP signal are measured near the visual cortex (i.e., near the back of the head of a user), SSVEP may be measured in other places as well. For instance, SSVEP signals may be measured near the neck, cheeks, nose bridge, etc. FIG. 6A illustrates various locations where electrodes may be located, according to one embodiment. As shown in FIG. 6A, electrodes for measuring SSVEP can also be placed near the ear 605 of a user. In particular, electrodes may be located behind the ear 610 of the user or near the temple 612 of the user. Placing electrodes around the ear 605 of the user allow the electrodes to couple with the mastoid of the user.

Since generally, there is an area around the ear 605 of a user where hair is either not present or very sparsely present, an electrode placed near the ear 605 of a user may have better coupling to the skin of the user than an electrode placed in a region where hair is present. As a result, a sufficient coupling between the electrode and the skin of the user to obtain an SSVEP signal can be obtained without the use of a conductive gel. That is, in this manner, a dry electrode may be used to measure SSVEP signals.

Moreover, in some applications, electrodes may be placed in the nose area 614 of the user. For instance, an electrode may be placed on the nose bridge of the user. The electrode placed in the nose area 614 of the user may be a reference electrode for measuring SSVEP signals. In some embodiments, electrodes may be located on other regions of the user's head, such as, on the neck, cheeks, forehead, occipital region, and the like.

Figure 6B:
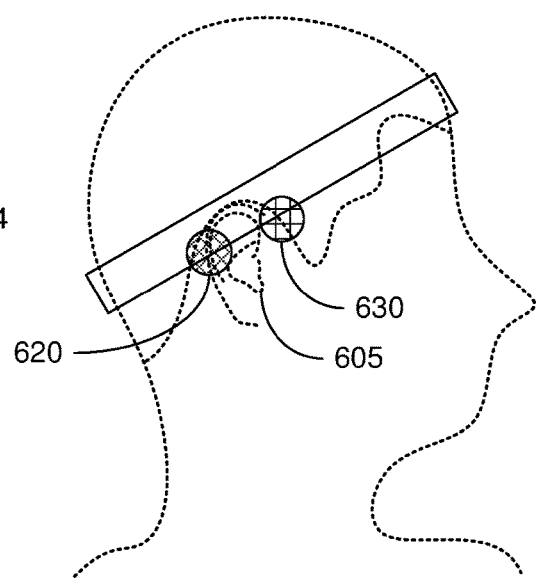
FIG. 6B illustrates a dry electrode configuration using a headband, in accordance with one or more embodiments.

In some embodiments, the electrodes may be embedded in a headband that wraps around the head of a user. The electrodes are placed on the headband such that when the user wears the headband, the electrodes are located either behind the ear 610 of the user or near the temple 612 of the user. FIG. 6B illustrates a dry electrode configuration using a headband, according to one embodiment. In the embodiment of FIG. 6B, the headband includes two electrodes 620, 630. A first electrode 630 may be a ground or reference electrode. The first electrode is located near the temple 612 of the user's head. The second electrode 620 is a recording electrode that measures SSVEP signals. The second electrode 620 is located behind the ear 610 of the user. In some embodiments, the headband includes electrodes around both ears of the user. For example, the headband may include four electrodes, two in each side of the user's head. On the first side, the headband may include a reference electrode and a first recording electrode. On the second side, the headband may include a ground electrode and a second recording electrode. In some embodiments, the headband includes a ground and/or a reference electrode on one side, and a recording electrode on the other side.

Figure 6C:
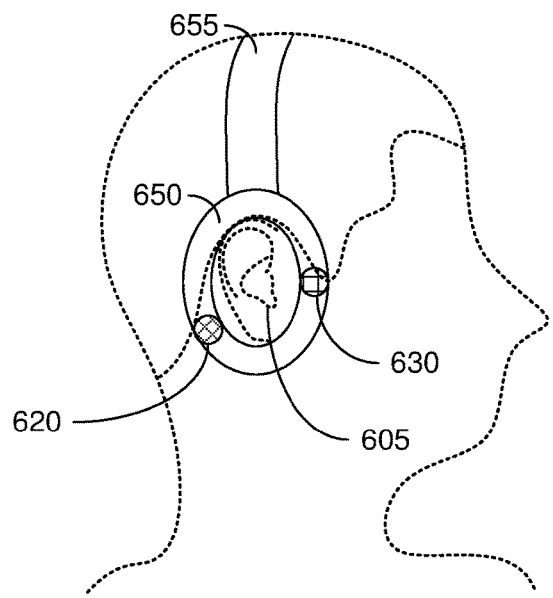
FIG. 6C illustrates a dry electrode configuration using headphones, in accordance with one or more embodiments.

FIG. 6C illustrates a dry electrode configuration using headphones, according to one embodiment. Since when in use, headphones are located around the ear 605 of a user, electrodes for measuring SSVEP signals can be embedded on the earcups 650 of the headphones. In one embodiment, the electrodes are embedded on the ear cushion or earpads of the earcups 650. In the embodiment of FIG. 6C, one earcup 650 has a first electrode 630 and a second electrode 620. The first electrode 630 may be a ground or reference electrode. The second electrode 620 may be a recording electrode. In some embodiments, the earcup 650 may include additional electrodes. For example, the earcup 650 may include multiple recording electrodes.

In some embodiments, the earcup 650 is detachable to allow a user to replace the ear cushions with additional ear cushions that have different electrode configurations. Ear cushions may have different electrode configurations that are designed for different head shapes or different applications. The ear cushions and the earcup may have electrodes that connect the electrodes embedded in the ear cushions to the circuitry for operating the electrodes.

In some embodiments, the headphone can be configured to adjust the pressure the earcups apply to the head of the user. For example, the headphone includes an adjustable headband 655 that connects the left and right earcups 650 together. The adjustable headband 655 may be adjusted increase or decrease the amount of pressure the left and right earcups 650 apply to the head of the user. The adjustable headband 655 may be expanded to decrease the pressure applied or contracted to increase the pressure applied. The amount of pressure applied by the earcups help secure the earcups 650 to the head of the user, improves sound isolation to prevent ambient noise to be heard by the user, and improves the contact between the electrodes 620, 630 and the skin of the user.

Figure 6D:
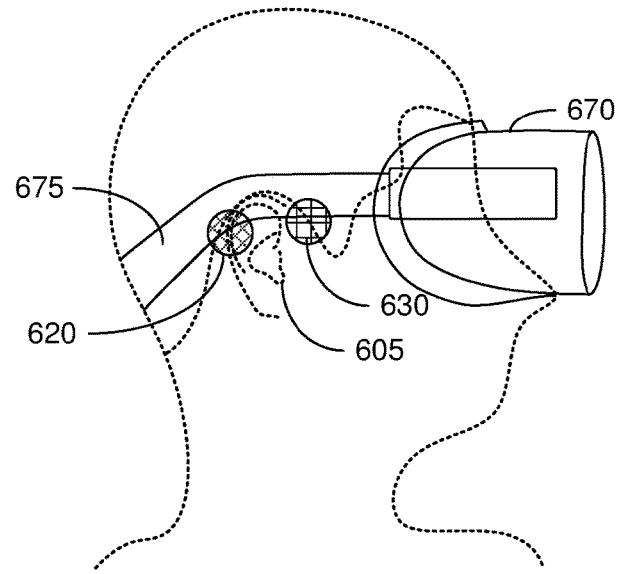
FIG. 6D illustrates a dry electrode configuration using a VR or AR headset, in accordance with one or more embodiments.

FIG. 6D illustrates a dry electrode configuration using a VR or AR headset, according to one embodiment. The headset includes a head-mounted display (HMD) 670 and a strap 675. In some embodiments, the headset uses temples or arms instead of straps 675. The HMD may be opaque or translucent. For instance, a VR headset may use an opaque HMD, whereas an AR headset may use a translucent HMD. The strap 675 secures the HMD 670 in place by wrapping around the head of the user. Electrodes 620, 630 may be embedded on or attached to the strap 675 such that, when worn by a user, the electrodes 620, 630 are located near the ear 605 of the user. The electrodes may include a first electrode 630 and a second electrode 620. The first electrode 630 may be a ground or reference electrode. The second electrode 620 may be a recording electrode.

In some embodiments, additional electrodes are included on the HMD such that the electrodes are in contact with the user's skin in the nose area 614. The electrode configured to contact the user's skin in the nose area 614 may be embedded in a nosepiece of the HMD. In some embodiments, the electrode in the nose area 614 is a reference electrode. In some embodiments, the HMD may include additional electrodes. For example, the HMD may include electrodes placed on the cheeks of the user.

By using dry electrodes with improved coupling and signal to noise ratio (SNR), higher frequencies stimuli may be employed. For example, stimuli about 45 Hz may be employed such that the stimuli are not visually perceived by the user, while still being able to detect an SSVEP signal.

8. Conclusion

The foregoing description of the embodiments has been presented for the purpose of illustration; it is not intended to be exhaustive or to limit the patent rights to the precise forms disclosed. Persons skilled in the relevant art can appreciate that many modifications and variations are possible in light of the above disclosure.

Some portions of this description describe the embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the patent rights. It is therefore intended that the scope of the patent rights be limited not by this detailed description, but rather by any claims that issue on an application based hereon. Accordingly, the disclosure of the embodiments is intended to be illustrative, but not limiting, of the scope of the patent rights, which is set forth in the following claims.

What is claimed is:

1. A system comprising:
an eye tracking device including an eye imaging sensor, wherein the eye tracking device is operable to transmit data derived from the eye imaging sensor;
a wearable interface worn at a head region of a user, the wearable interface including a plurality of electrodes operable to measure signals evoked by visual stimuli that the user is looking at, wherein the wearable interface is operable to transmit data derived from the signals;
an electronic display including a plurality of pixels operable to display a plurality of objects using the plurality of pixels; and
a client device operable to receive data from the eye tracking device and the wearable interface, the client device configured to:
determine, using the data received from the eye tracking device, a gaze region of the user on the electronic display;

identify a subset of objects of the plurality of objects represented by pixels of the plurality of pixels within the gaze region on the electronic display;

responsive to identifying the subset of objects, display a visual stimulus for each object of the subset of objects on the electronic display by altering the pixels representing each object, wherein each visual stimulus has a unique frequency relative to the visual stimuli for other objects of the subset of objects;

receive a visually evoked signal from the wearable interface;

compare a frequency derived from the visually evoked signal to the frequency of each visual stimulus of the subset of objects;

identify, based on the comparison, an object of the subset of objects corresponding to a visual stimulus having a frequency that matches the frequency derived from the visually evoked signal; and execute a set of instructions associated with the identified object.

2. The system of claim 1, wherein the electronic display, the eye tracking device, and the wearable interface are components of a virtual reality headset.

3. The system of claim 1, wherein the electronic display, the eye tracking device, and the wearable interface are components of an augmented reality headset.

4. The system of claim 1, wherein the client device is further configured to:
determine a user gaze direction using the data received from the eye tracking device, wherein the gaze direction approximates where the user is looking;
map the gaze direction to a position on the electronic display; and
determine the gaze region using the position on the electronic display, the gaze region encompassing the position on the electronic display.

5. The system of claim 1, wherein one or more electrodes of the plurality of electrodes are dry electrodes.

6. The system of claim 1, wherein the plurality of electrodes comprises a reference electrode and a recording electrode, the wearable interface measures the visually evoked signal between the recording electrode and the reference electrode.

7. The system of claim 1, wherein the gaze region is determined based on a field of view of the user.

8. The system of claim 1, wherein the visually evoked signal is a plurality of steady state visually evoked potentials measured by a plurality of electrodes of the wearable interface.

9. The system of claim 1, wherein the client device is further configured to:
determine a number of objects in the subset of objects;
select a set of frequencies based on a refresh rate of the electronic display and the determined number of objects;
assign a different frequency from the selected set of frequencies to each of the objects in the subset of objects; and
alter the pixels representing each of the objects in subset of objects based on the assigned frequencies.

10. The system of claim 1, wherein the client device is further configured to:
responsive to identifying an object of the subset of objects corresponding to the visual stimulus, stop the display of the visual stimulus.

11. A method performed by a client device comprising:
receiving a user gaze direction from an eye tracking device, wherein the gaze direction approximates where a user of the client device is looking;
mapping the gaze direction to a position on an electronic display including a plurality of pixels, the plurality of pixels representing a plurality of objects;
determining a gaze region on the electronic display encompassing the mapped position;
identifying a subset of objects of the plurality of objects represented by pixels of the plurality of pixels within the gaze region on the electronic display;
responsive to identifying the subset of objects, displaying a visual stimulus for each object of the subset of objects by altering the pixels representing each object, wherein each visual stimulus has a unique frequency relative to the visual stimuli for other objects of the subset of objects;
receiving a visually evoked signal from a wearable interface worn by a user, the visually evoked signal measured by the wearable interface at a head region of the user;
comparing a frequency derived from the visually evoked signal to the frequency of each visual stimulus of the subset of objects;
identifying, based on the comparison, an object of the subset of objects corresponding to a visual stimulus having a frequency of the object that matches the frequency derived from the visually evoked signal; and
executing a set of instructions on the client device associated with the identified object.

12. The method of claim 11, wherein the gaze region is determined based on a field of view of the user.

13. The method of claim 11, wherein the visually evoked signal is a plurality of steady state visually evoked potentials measured by a plurality of electrodes on the wearable interface.

14. The method of claim 11, wherein displaying the visual stimulus for each object comprises:
determining a number of objects in the subset of objects;
selecting a set of frequencies based on a refresh rate of the electronic display and the determined number of objects;
assigning a different frequency from the selected set of frequencies to each of the objects in the subset of objects; and
altering the pixels representing each of the objects in the subset of objects based on the assigned frequencies.

15. The method of claim 11, further comprising:
responsive to identifying an object of the subset of objects corresponding to the visual stimulus, stopping the display of the visual stimulus.

16. The method of claim 11, wherein displaying a visual stimulus comprises altering the pixels representing one or more objects of the subset of objects to display a pattern including a solid color, a polychromatic spiral, or a checkerboard.

17. The method of claim 11, wherein the frequency of one or more of the visual stimuli corresponds to a rate at which the pixels representing one or more objects of the subset of objects corresponding to the one or more visual stimuli alternate between a first color and a second color.

18. The method of claim 11, wherein the frequency of one or more of the visual stimuli corresponds to a rate at which the one or more visual stimuli rotate.

19. The method of claim 11, wherein determining the derived frequency comprises:
   computing, for each template of a set of signal templates, a correlation between the visually evoked signal and the template, wherein each template corresponds to a distinct frequency; and
   selecting a frequency corresponding to a template from the set of signal templates having a highest correlation as the derived frequency.

20. The method of claim 11, wherein the frequency derived from the visually evoked signal is determined based on a plurality of signals measured at a plurality of electrodes on the wearable interface.

* * * * *

UNITED STATES PATENT AND TRADEMARK OFFICE
CERTIFICATE OF CORRECTION

| | |
|---|---|
| PATENT NO. | : 11,093,033 B1 |
| APPLICATION NO. | : 16/666282 |
| DATED | : August 17, 2021 |
| INVENTOR(S) | : Wang et al. |

It is certified that error appears in the above-identified patent and that said Letters Patent is hereby corrected as shown below:

In the Claims

Column 17, Line 43, Claim 6, delete "electrode," and insert -- electrode, and wherein --.

Column 18, Lines 15-16, Claim 11, delete "objects by" and insert -- objects on the electronic display by --.

Column 18, Line 29, Claim 11, delete "frequency of the object" and insert -- frequency --.

Signed and Sealed this
Third Day of May, 2022

Katherine Kelly Vidal
*Director of the United States Patent and Trademark Office*